United States Patent [19]

Strumwasser et al.

[11] Patent Number: 5,202,426
[45] Date of Patent: Apr. 13, 1993

[54] EUCARYOTIC NAD CYCLASES

[75] Inventors: Felix Strumwasser, Falmouth; Mark R. Hellmich, Woods Hole; David L. Glick, Falmouth, all of Mass.

[73] Assignee: Marine Biological Laboratory, Woods Hole, Mass.

[21] Appl. No.: 629,101

[22] Filed: Dec. 17, 1990

Related U.S. Application Data

[63] Continuation-in-part of Ser. No. 404,733, Sep. 8, 1989, abandoned, which is a continuation-in-part of Ser. No. 266,145, Nov. 2, 1988, abandoned.

[51] Int. Cl.$^5$ .............................................. C12N 15/60
[52] U.S. Cl. .................................. 536/23.2; 435/232; 536/26.13
[58] Field of Search ..................... 435/232, 69.1; 536/27

[56] References Cited

PUBLICATIONS

Chem. Abstract No. 105:55579n, Kim et al. 1986 Han'-guk Saenghwa Hakhoechi 19(1):32–40.
Sofer et al. 1983, Bio Techniques, Nov./Dec., pp. 198–203.
Alberti, B. 1983, *Molecular Biology of the Cell*, Garland Publishing Inc., New York, N.Y., pp. 185–196.
Lee et al. 1991, Cell Regulation 2:203–209.
Swislocki et al., The Journal of Biological Chemistry, vol. 242(6):1089–1094, 1967.
Swislocki and Kaplan, the Journal of Biological Chemistry, vol. 242(2):1084–1088, 1967.
Yuan and Anderson, The Journal of Bilogical Chemistry, vol. 246(7):2111–2115, 1971.
Yost and Anderson, The Journal of Biological Chemistry, vol. 256(8):3647–3653, 1981.
Stathakos et al., Biochimica et Biophysica Acta 301 (1973) 80–89.
Wolf et al., J. Biochem., 226:415–427, 1985.
Moss et al., The Journal of Biological Chemistry, vol. 257(1):5755, 1982.
Kim et al., Biochimica et Biophysica Acta 965 (1988) 76–81.
Lee et al., The Journal of Biological Chemistry, vol. 264(3):1608–1615, 1989.
Clapper et al., The Journal of Biological Chemistry, vol. 262(20):9561–9568, 1987.
Rusinko and Lee, The Journal of Biological Chemistry, vol. 264(20):11725–11731, 1989.
Dargie et al., Cell Regulation, vol. 1:279–290, 1990.
Pekala et al., Academic Press, Inc. pp. 325–377, 1982.
Amar-Costesec et al., J. Cell Biology, vol. 100, pp. 189–197, 1985.
Schuber et al., Eur. J. Biochem., vol. 69, pp. 593–602, 1976.
Bitonti, Biochemical and Biophysical Research Communications, vol. 120(2):700–706, 1984.
Lapetina et al., Proc. Natl. Acad. Sci. USA, 83:5880, 1986.
Hsia et al., The Journal of Biological Chemistry, 259(2):1086, 1983.
Ward et al., Biochemical and Biophysical Research Communications, 105:928, 1982.
Owens et al., J. Biological Chemistry, 260:15946, 1985.
Gillman, Ann. Rev. Biochem. 56:615–49, 1987.
Ribeiro-Neto et al., Methods in Enzymology, 109:566, 1985.
Middlebrook et al., Microbiological Reviews, 48:199, 1984.
Katada et al., J. Biological Chemistry, 257:7210, 1982.
Katada et al., Proc. Natl. Acad. Sci, USA 97:3129, 1982.
Milligan The Biochemical Journal, 255, No. 1, 1988.
Laemmli, Nature, 227:680, 1970.
Gill et al., Proc. Natl. Acad. Sci, USA, vol. 75(7):3050–3054, 1978.
Rothenberg et al., J. Biological Chemistry 269:15540, 1988.
Hara-Yokoyama et al., FEB Letters 05984, vol. 234, No. 1, 27–30, 1988.

*Primary Examiner*—Robert A. Wax
*Assistant Examiner*—Keith C. Furman
*Attorney, Agent, or Firm*—Lyon & Lyon

[57] ABSTRACT

Eucaryotic NAD cyclases able to cause production of cyclic adenosine diphosphate ribose from nicotinamide adenine dinucleotide.

1 Claim, 5 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 23
        ( B ) TYPE: nucleic acid
        ( C ) STRANDEDNESS: single ( i x ) FEATURE:
        ( D ) OTHER INFORMATION: The letter "N"stands for
                                        inosine (i).

( x i ) SEQUENCE DESCRIPTION: SEQ ID NO: 1:

```
TATGATGAAG CNCATGATTA TGC         23
    C   C   G        G  C    C
```

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
                                        inosine (i).

( x i ) SEQUENCE DESCRIPTION: SEQ ID NO: 2:

```
TGTAAAGATT ATGAAATNAC             20
    C   G       C   C  G
```

( 2 ) INFORMATION FOR SEQ ID NO: 3:

( i ) SEQUENCE CHARACTERISTICS:
        ( A ) LENGTH: 1191
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
GATTTAGAA                                                                        9

ATG TCT CCC GTC GCC ATT ATT GCT TGT GTG TGT CTG GCG GTG ACG CTG                 57
Met Ser Pro Val Ala Ile Ile Ala Cys Val Cys Leu Ala Val Thr Leu
                 5               10              15

ACA AGT ATC TCG CCC AGC GAG GCC ATC GTC CCC ACT CGC GAG TTG GAG                105
Thr Ser Ile Ser Pro Ser Glu Ala Ile Val Pro Thr Arg Gle Leu Glu
             20              25              30

AAT GTG TTC CTT GGC CGC TGT AAG GAT TAC GAG ATC ACC CGA TAC CTG                153
Asn Val Phe Leu Gly Arg Cys Lys Asp Tyr Glu Ile Thr Arg Tyr Leu
         35              40              45

GAT ATT CTT CCC AGA GTG AGA TCG GAC TGC TCG GCA TTG TGG AAG GAC                201
Asp Ile Leu Pro Arg Val Arg Ser Asp Cys Ser Ala Leu Trp Lys Asp
     50              55              60

TTT TTC AAA GCC TTC TCC TTC AAA AAT CCC TGT GAT CTC GAC CTT GGA                249
Phe Phe Lys Ala Phe Ser Phe Lys Asn Pro Cys Asp Leu Asp Leu Gly
65              70              75              80

AGT TAC AAA GAT TTT TTC ACT AGT GCG CAA CAG CAG CTG CCA AAG AAC                297
Ser Tyr Lys Asp Phe Phe Thr Ser Ala Gln Gln Gln Leu Pro Lys Asn
             85              90              95

AAA GTA ATG TTC TGG TCT GGA GTC TAT GAC GAG GCT CAC GAT TAT GCC                345
Lys Val Met Phe Trp Ser Gly Val Tyr Asp Glu Ala His Asp Tyr Ala
         100             105             110

AAC ACC GGC AGG AAG TAC ATC ACT TTG GAA GAT ACG CTT CCG GGT TAC                393
Asn Thr Gly Arg Lys Tyr Ile Thr Leu Glu Asp Thr Leu Pro Gly Tyr
     115             120             125

ATG TTG AAC TCT CTG GTT TGG TGC GGC CAA CGC GCT AAT CCA GGA TTC                441
Met Leu Asn Ser Leu Val Trp Cys Gly Gln Arg Ala Asn Pro Gly Phe
```

|  |  |  |  |  |  |  |  |  |  |  |  |  |  |  |  |
|---|---|---|---|---|---|---|---|---|---|---|---|---|---|---|---|
| 130 | | | | | 135 | | | | | 140 | | | | | |
| AAC | GAA | AAG | GTG | TGC | CCG | GAC | TTC | AAA | ACG | TGT | CCA | GTG | CAA | GCT | AGA | 489
| Asn | Glu | Lys | Val | Cys | Pro | Asp | Phe | Lys | Thr | Cys | Pro | Val | Gln | Ala | Arg |
| 145 | | | | | 150 | | | | | 155 | | | | | 160 |

```
      GAG AGC TTC TGG GGA ATG GCG TCA AGT TCT TAT GCT CAC AGT GCA GAG        537
      Glu Ser Phe Trp Gly Met Ala Ser Ser Ser Tyr Ala His Ser Ala Glu
                      165                 170                 175

GGA GAA GTG ACC TAC ATG GTC GAC GGT TCG AAT CCC AAG GTA CCA GCT        585
      Gly Glu Val Thr Tyr Met Val Asp Gly Ser Asn Pro Lys Val Pro Ala
                      180                 185                 190

TAC AGG CCA GAC AGT TTT TTT GGC AAG TAC GAA CTG CCC AAT CTG ACT        633
      Tyr Arg Pro Asp Ser Phe Phe Gly Lys Tyr Glu Leu Pro Asn Leu Thr
                      195                 200                 205

AAC AAG GTG ACA AGG GTA AAG GTC ATC GTC CTG CAT CGG CTC GGG GAA        681
      Asn Lys Val Thr Arg Val Lys Val Ile Val Leu His Arg Leu Gly Glu
                      210                 215                 220

AAG ATC ATA GAG AAG TGC GGT GCA GGA TCT TTG CTG GAC CTT GAA AAG        729
      Lys Ile Ile Glu Lys Cys Gly Ala Gly Ser Leu Leu Asp Leu Glu Lys
      225                 230                 235                 240

CTT GTC AAA GCC AAG CAT TTT GCA TTC GAT TGC GTG GAA AAT CCA AGG        777
      Leu Val Lys Ala Lys His Phe Ala Phe Asp Cys Val Glu Asn Pro Arg
                      245                 250                 255

GCT GTT CTC TTC TTG CTG TGC TCC GAC AAC CCC AAT GCC AGA GAG TGT        825
      Ala Val Leu Phe Leu Leu Cys Ser Asp Asn Pro Asn Ala Arg Glu Cys
                      260                 265                 270

CGA CTC GCT AAA CGT TTC TAC AGG ATC GCC                                855
      Arg Leu Ala Lys Arg Phe Tyr Arg Ile Ala
                      275                 280

TAAATAATCC AGCACCGCTC GTCAACTATT TAAGAGGCGT TTCGTTAGAG GTTTATAAAT           915

TAATTCTTTT TTTTGAGAA CGTGTCGACG GTGGCAAAAT GGGGTCGTTT TTTTAGTCAT            975

TAGTGTTGGA AAATATATTG GGGATAAAAA TGGGGTGGGG CTGGGGCATT GCTGTTGACG          1035

ATATAAAGTA AAGAGGGAGG GGGCAGCTCT TCACTTCAGT GCGCACAGCA GTTGTTATGA          1095

ATTGAGGGCT GAACGTTCTC GAGTACATTT CAATATTAAC TTCTTGATGT AGAGAGGGTA          1155

CGCTCTTTAC CAATTTCAAA TTATTTAAAA GGTGTG                                   1191
```

EUCARYOTIC NAD CYCLASES

This invention was made with U.S. Government support, specifically, N.I.H. grant number NS21046. The U.S. Government has certain rights in the invention.

BACKGROUND OF THE INVENTION

This application is a continuation-in-part of Strumwasser et. al., U.S. Ser. No. 404,733, filed Sep. 8, 1989, now abandoned, entitled EUCARYOTIC NADases, which is a continuation-in-part of Strumwasser et al., U.S. Ser. No. 266,145 filed Nov. 2, 1988, now abandoned, entitled "Bacterial Toxin Inhibitory Factor", both of which are hereby incorporated by reference herein (including the drawings therein).

The invention concerns eucaryotic NADases having NAD cyclase activity.

Moss et al., *Journal of Biological Chemistry*, 257:5755-5759, 1982, describe rat liver NAD glycohydrolase having a molecular weight of approximately 67,000, and a Km of about 18 $\mu$M.

Swislocki et al., *Journal of Biological Chemistry*, 242:1089-1094, 1967, describe various diphosphopyridine nucleosidases of molecular weight of approximately 25,000, 50,000, and between 70,000, and 90,000. These enzymes are present in porcine, bovine, and sheep.

Swislocki and Kaplan, *Journal of Biological Chemistry*, 242:1083-1088, 1967, describe purification of diphosphopyridine nucleosidase from pig brain. This enzyme has a molecular weight of 26,000.

Yuan and Anderson, *Journal of Biological Chemistry*, 246:2111-2115, 1971, describe bull serum nicotinamide adenine dinucleotide nucleosidase.

Yost and Anderson, *Journal of Biological Chemistry*, 256:3647-3653, 1981 describe the purification of soluble NAD glycohydrolase from *Bungarus fasciatus* venom.

Stathakos et al., *Biochimica et Biophysica Acta*, 302:80-89, 1973 describe purification of NAD nucleosidase from *Fusarium nivale*.

De Wolf et al., *Biochem. J.*, 226:415-427, 1985 describe purification of thyroidal NAD glycohydrolase.

Kim et al., *Biochimica et Biophysica Acta*, describe an NAD glycohydrolase from rabbit erythrocytes.

SUMMARY OF THE INVENTION

Applicants have discovered a family of eucaryotic NAD cyclases having an enzymatic activity which converts nicotinamide adenine dinucleotide (NAD) to cyclic adenosine diphosphate ribose (cADPR). While such activity has been known in the art, applicants are the first to identify individual proteins having such activity and to provide those proteins in an enriched and purified form. This discovery allows production of a purified NAD cyclase having the above-described activity and thus provides a method for making purified cADPR in large amounts. Prior to applicants discovery, cADPR was available only in extremely small amounts and as a crude preparation. See Lee et al., *J. Biological Chemistry*, 264:1608-1615, 1989, Clapper et al., *J. Biological Chemistry*, 262:9561-9568, 1987, Rusinko and Lee, *J. Biological Chemistry*, 264:11725-11731, 1989, and Dargie et al., *Cell Regulation*, 1:279-290, 1990.

Thus, the invention features, in various related aspects, a purified NAD cyclase which causes production of cADPR from NAD; a method for production of purified cADPR by contacting that purified NAD cyclase with NAD under appropriate conditions; and the resulting purified cADPR.

By "purified cADPR" is meant that the cADPR is provided in a form which when passed over a high pressure liquid chromatography column shows little or no contamination by components other than NAD and ADP-R (adenosine diphosphate ribose). An example of such a pure preparation is shown in FIG. 5, where cADPR is provided at greater than 85% purity. This compares to the impure cADPR described by Lee et al., supra where significant contamination exists (see FIG. 1 of Lee et al., supra). In addition, the cADPR is provided in amounts in excess of a few nanograms, it is provided in $\mu$g or mg quantities in a purified state. Thus, the cADPR is provided separated from cellular components which are present when the cADPR is isolated after incubation with a crude tissue extract. In this invention such cADPR is produced generally by treatment with a recombinantly expressed or otherwise purified NAD cyclase.

In a related aspect, the invention features a composition enriched for a eucaryotic NAD cyclase including a protein which is present in the aqueous extract of a gonad of a marine mollusc. The NAD cyclase has the above-described enzymatic activity which cause cADPR production from NAD. Preferably, the protein, or NAD cyclase, has an extremely high NAD cyclase activity such that 1 $\mu$g of NAD cyclase is able to remove sufficient NAD in a reaction solution to thereby indirectly reduce the transferase activity of 0.28 $\mu$g of the ADP-ribosyl transferase of cholera toxin by at least 90% of the natural activity.

By "enriched" is meant that the NAD cyclase is separated from the immediate cellular environment in which it naturally occurs, and is purified from one or more components in that environment, rendering it useful as described herein. Preferably, the NAD cyclase is provided as a homogeneous solution and is produced by recombinant DNA technique. The NAD cyclase indirectly reduces the specific activity of an ADP-ribosyl transferase in any standard assay for such a transferase, for example, as described below in Description of the Preferred Embodiments. By "protein" is meant any organic macromolecule which includes a polypeptide sequence of at least about 30 amino acids, being either a polypeptide, glycosylated polypeptide or other modified polypeptide. BY "indirectly reduce the activity" is meant that the NAD cyclase reduces transferase activity by removing NAD required for the activity. The phrase "present in" is not meant to be limiting in this invention; it indicates only that the NAD cyclase, or its equivalent, is present in the marine mollusc, not that the NAD cyclase must be isolated from that mollusc.

In preferred embodiments of the invention, the mollusc belongs to the genus Aplysia; and the NAD cyclase a) has an apparent molecular weight in an SDS-polyacrylamide gel of 24,000-34,000 under reducing conditions; b) is stained by Coomassie blue; c) binds to a cation-exchange resin equilibrated at pH 8, e.g., a CM-SEPHAROSE-Cl-6B cation exchange resin, and is eluted from that resin in 300-400 mM NaCl; d) elutes from a gel filtration column, e.g., a SEPHACRYL S-200 gel filtration column in a 50-75% column fraction; e) is inactivated by heating at 70° C. for 15 minutes; and f) is present in a soluble fraction of gonad, and is purified more than 500 fold by passage over a cation-exchange column. In other preferred embodiments, the NAD cyclase has an IC$_{50}$ of between 0.4 and 1 nanoMolar for cholera toxin.

In a further related aspect, the invention features a purified NAD cyclase which causes production of cADPR from NAD. Preferably, the NAD cyclase also indirectly inhibits the ADP-ribosyl transferase of cholera toxin, 1 μg of the NAD cyclase reducing the activity of 0.28 μg of the transferase by at least 90%. In addition, the NAD cyclase has an amino acid sequence having at least 90% sequence similarity to a contiguous 30 amino acid or greater sequence of an NAD cyclase present in *Aplysia californica* having an apparent molecular weight of 24,000–34,000 in an SDS-polyacrylamide gel under reducing conditions.

By "purified" is meant that the NAD cyclase is isolated from the immediate cellular environment in which it naturally occurs, and is separated from one or more components with which it is naturally associated, rendering it useful as described herein. The NAD cyclase may be a naturally occurring NAD cyclase which has been purified from its natural environment, or it may be expressed by standard genetic manipulation of a gene encoding the NAD cyclase, or by synthesis of oligonucleotides which encode the NAD cyclase. It may also be any equivalent NAD cyclase, i.e., one produced by genetic engineering to have similar enzymatic activity but slightly different amino acid sequence. Those skilled in the art will recognize that proteins with such slight differences are readily made using standard techniques and that the engineered differences have little, if any, affect on the NADase or NAD cyclase activity of the resulting NAD cyclase. Similarly, the NAD cyclase, or its equivalent, may be synthesized by standard polypeptide synthesis.

In preferred embodiments, the NAD cyclase naturally occurs in an invertebrate animal, most preferably in a mollusc, e.g., of the genus Aplysia.

In another related aspect, the invention features purified nucleic acid encoding a eucaryotic NAD cyclase which causes production of cADPR from NAD. Preferably, it also indirectly inhibits the ADP-ribosyl transferase activity of cholera toxin, 1 μg of the NAD cyclase reducing the activity of 0.28 μg of the transferase by at least 90%.

By "purified" in this case is meant that the nucleic acid is isolated from its natural nuclear genomic environment, and preferably that it is present within any standard vector, or is positioned within a genome of a cell in which it does not naturally occur. It also means that the nucleic acid is present in a preparation homogeneous enough to be useful for cloning or manipulation to produce a useful cell or vector able to express the NAD cyclase. Such nucleic acid is thereby rendered useful as described herein. Thus, this term does not encompass isolated total genomic DNA of a eucaryotic cell, nor a library of clones (one of which may encode the NAD cyclase). Rather it includes isolated clones or DNA fragments identified as having the desired nucleic acid which can be used to express the NAD cyclase, or manipulated to cause such expression.

In preferred embodiments, the nucleic acid encodes an NAD cyclase having an amino acid sequence having at least 90% sequence similarity to a contiguous 30 amino acid sequence or greater of an NAD cyclase present in *Aplysia californica* having an apparent molecular weight of 24,000–34,000 in an SDS-polyacrylamide gel under reducing conditions; and the nucleic acid includes a sequence of 20 contiguous base pairs identical to a naturally occurring nucleic acid sequence encoding for an NAD cyclase present in *Aplysia californica* having an apparent molecular weight of 24,000–34,000 in an SDS-polyacrylamide gel under reducing conditions.

In another related aspect, the invention features an essentially purified NAD cyclase present in the water soluble fraction of a marine mollusc gonad. The NAD cyclase causes production of cADPR from NAD. Preferably, it also has the following characteristics: (a) it indirectly inhibits by at least 90% the transfer of ADP-ribose from NAD to a G protein substrate of a eucaryotic cell by cholera toxin, and (b) it indirectly inhibits by at least 90% the transfer of ADP-ribose from NAD to a G protein substrate of a eucaryotic cell by pertussis toxin.

By "essentially purified" is meant that the NAD cyclase is separated from at least 95% of immediate cellular components with which it naturally occurs on a weight by weight basis.

In preferred embodiments, the essentially purified NAD cyclase is further characterized in that the NAD cyclase has an apparent molecular weight in an SDS-polyacrylamide gel of 24,000–34,000 under reducing conditions; is stained by Coomassie blue; binds to a cation-exchange resin, e.g., CM-SEPHAROSE-Cl-6B cation exchange resin, equilibrated at pH 8, and is eluted from this resin by 300–400 mM NaCl; elutes from a gel filtration column, e.g., a SEPHACRYL S-200 gel filtration column in a 50–75% column volume; is inactivated by heating at 75° C. for 15 minutes; has an IC$_{50}$ between 0.4 and 1 nanoMolar for cholera toxin; and the NAD cyclase is present in the soluble fraction of gonad, and is purified more than 500 fold by passage over a cation-exchange column.

In a final related aspect, the invention features a method for purifying a eucaryotic NAD cyclase characterized by the ability to cause production of cADPR from NAD. The method includes solubilizing the NAD cyclase and passing the NAD cyclase over a cation exchange column.

In preferred embodiments, the column is CM-SEPHAROSE-Cl-6B cation exchange column and the NAD cyclase is eluted from the column with 300–400 mM NaCl; and the NAD is passed over a gel filtration column, e.g., a SEPHACRYL S-200 gel filtration column.

Applicants are the first to identify a eucaryotic NAD cyclase, to identify a eucaryotic NADase of such low molecular weight, and to isolate a gene encoding a eucaryotic NAD cyclase. Applicants are the first to enable production of a recombinant eucaryotic NAD cyclase, and of large quantities of a useful laboratory and therapeutic agent. Applicants are also the first to enable production of significant quantities of cADPR.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

NAD Cyclase

Figure 1:
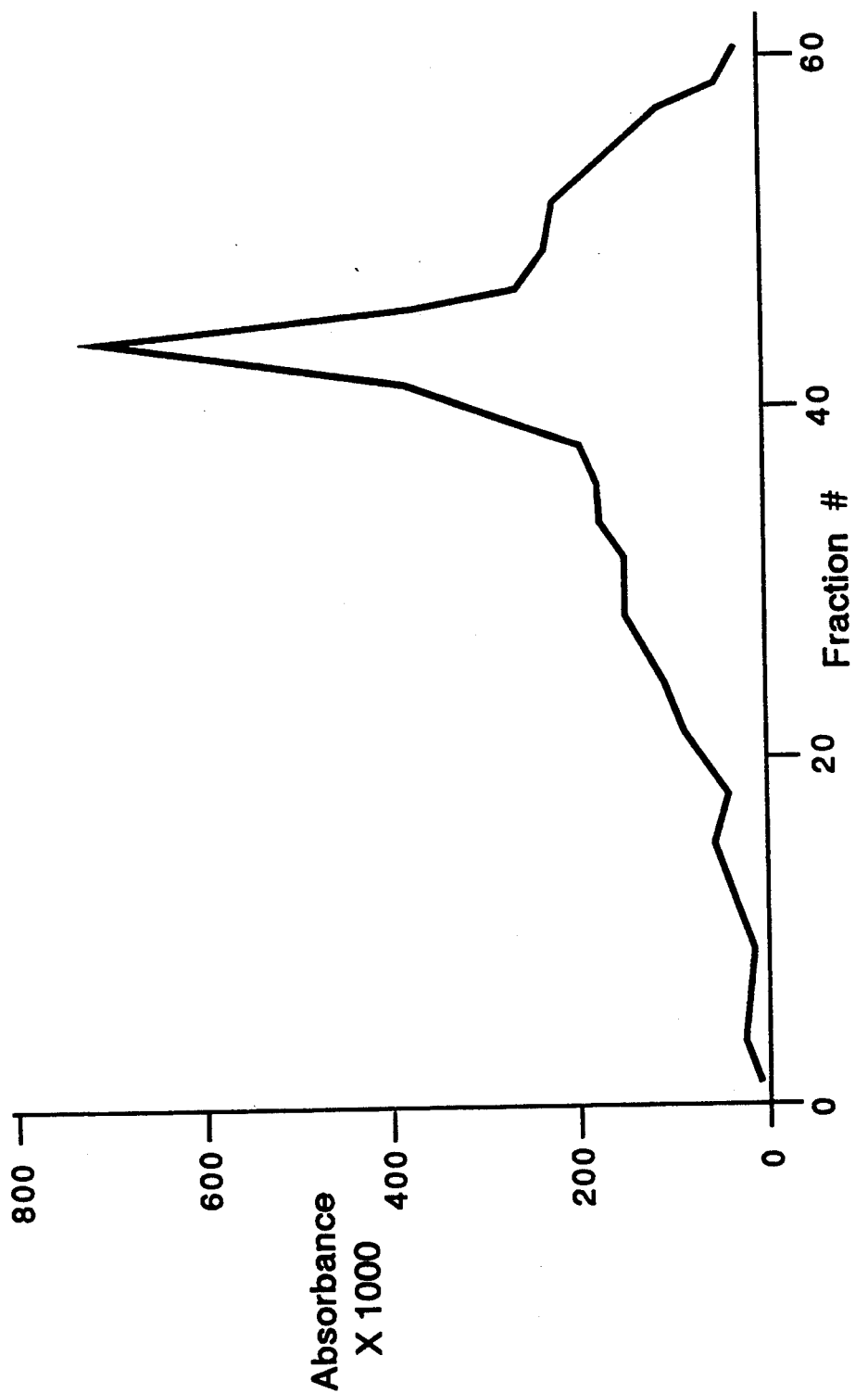
FIG. 1 is a graphical representation of the protein profile of fractions from a cation-exchange column.

NAD cyclases of this invention include NAD cyclases which cause production of cADPR from NAD. Such NAD cyclases also indirectly inhibit the ADP-ribosyl transferase activity of any protein, in particular the ADP-ribosyl transferase activity of a bacterial toxin, such as pertussis toxin or cholera toxin. 1 µg of these NAD cyclases indirectly reduce the activity of 0.28µg of a transferase by at least 90%, generally they completely inhibit such activity. These NAD cyclases appear to be resistant to two inhibitors of eucaryotic NAD cyclases, namely isonicotinic acid hydrazide and 3-acetylpyridine adenine dinucleotide. These NAD cyclases are also generally resistant to 1 mM DTT.

These NAD cyclases can be identified as naturally occurring NAD cyclases in living organisms by assaying for inhibitory effect in a standard ADP-ribosylation assay, e.g., as described below. The NAD cyclase can then be purified by standard techniques, the amino acid sequence of the NAD cyclase determined, and the gene encoding the NAD cyclase isolated. Thus, this invention includes not only naturally occurring NAD cyclases, or fragments thereof which include the NAD cyclase activity, but also includes synthetic polypeptides having such inhibitory activity, and polypeptides obtained by genetic manipulation of nucleic acid encoding for such polypeptides. This nucleic acid can be derived from the naturally occurring gene, or produced by standard synthetic procedures. Those NAD cyclases having cADPR-producing activity can be identified by incubation with NAD and detection of cADPR, as described below, or by any other standard technique.

There follows one example of such an NAD cyclase isolated from the invertebrate mollusc *Aplysia californica*. This example is not limiting to the present invention, and those skilled in the art will recognize that many other NAD cyclases can be isolated by similar techniques, or by related techniques, all of which are well known in the art.

EXAMPLE

NAD Cyclase from *Aplysia californica*

Aplysia were obtained from Alacrity Marine Biological Services (Redondo Beach, Calif.) and Sea Life Supply (Sand City, Calif.). The gonad (or ovotestis) of Aplysia was isolated and either placed directly into liquid nitrogen for storage and later use, or placed into ice-cold homogenization buffer (250 mM Sucrose, 20 mM HEPES buffer, pH 8.0, 1 mM EDTA, 1 mM DTT (dithiothreitol), 1 µg/ml leupeptin, 1 µg/ml soybean trypsin inhibitor, 1 mM phenylmethylsulfonylfluoride) and homogenized. The ratio of buffer volume to tissue wet weight varied from 5-80:1. Homogenization was performed with a glass on glass Dounce homogenizer or a Brinkman Polytron unit. The homogenized tissue was subjected to a low speed centrifugation (20,000×g for 20 minutes, 4° C.) and the supernatant subsequently centrifuged (150,000×g, 90-120 min, 4° C.). The supernatant of the high speed spin is referred to as the aqueous soluble, or just "soluble", fraction while the pellet is termed the "membrane" fraction.

The soluble fraction was diluted with a cation-exchange column equilibration buffer (20 mM HEPES buffer, pH 8.0, 250 mM Sucrose, 1 mM EDTA, 1 mM DTT) until its conductivity was equivalent to that of the buffer. For cation-exchange chromatography, a CM-SEPHAROSE-Cl-6B cation exchange resin (Pharmacia) was equilibrated with the above equilibration buffer and the diluted soluble fraction of gonad applied. After a one column volume wash with equilibration buffer, a continuous NaCl gradient (0-500 mM) was applied to the column and fractions collected. The peak of NAD cyclase activity was pooled, concentrated, and applied to a SEPHACRYL-S200 (Pharmacia) gel filtration column. Fractions from this column and other fractions were assayed as follows.

For both cholera toxin (CT) and pertussis toxin (PT) ADP-ribosyl transferase NAD cyclase assays the CT (Calbiochem or List Biological) and PT (List Biological) were activated in 10 mM DTT for 30 min. at 32° C. just prior to incubation with tissue. In each assay the amount of protein used for ADP-ribosylation was made equal (15-50 µg, as determined with the Pierce Chemical Co., (Rockford, Ill.) protein assay reagent).

For CT-catalyzed ADP-ribosylation, the assay was a modification of Ribeiro-Neto et al., supra. Briefly, 20 µl (15-50 µg total protein) of soluble or membrane fraction of Aplysia tissue which contained various G-proteins (prepared as described above for Aplysia gonad, except that 50 mM HEPES pH 7.6 was used in place of 20 mM HEPES buffer, pH 8.0 in the homogenization buffer) was added to 40 µl of reaction mixture (0.28 µg/µl (i.e., at 13.2µ Molar) of activated CT, 1 µCi $^{32}$P-NAD, 10 µM NAD, 25 mM Tris-HCl buffer, pH 7.5, 10 mM thymidine, 20 mM ADP-ribose, 300 mM potassium phosphate, 1 mM ATP, 10 mM magnesium chloride, 0.5 mM GppNHp or GTP, and 1 mM EDTA). This mixture was incubated for 45 min. at 30°-32° C. and the reaction stopped by the addition of 1 ml of ice-cold 20% TCA. After a minimum of two hours on ice, the mixture was spun in an EPPENDORF centrifuge at 4° C. for 20 min. The pellet was washed with 1.5 ml of ether and respun. The pellet was then air dried and dissolved in 40 µl of 2× Laemmli's (227 Nature 680, 1970) sample buffer.

For PT-catalyzed ADP-riboslyation the assay was identical to that for CT, except that the reaction mixture consisted of: 3 µg of activated PT, 1 µCi $^{32}$P-NAD, 10 µM NAD, 100 mM Tris-HCl buffer, pH 8.0, 5 mM thymidine, 0.5 mM ADP-ribose, 2.5 mM ATP, 4 mM magnesium chloride, 1 mM GTP, and 2 mM EDTA.

When column fractions were tested for NAD cyclase, the only change in the ADP-ribosylation procedure was addition of 10 µl of the column fraction to 10 µl of the soluble or membrane fraction.

Samples from the above assays were electrophoresed on standard SDS-polyacrylamide slab gels (12% acrylamide, see e.g., Gill, supra). Molecular weight standards used spanned the range of 14,000-66,000. For autoradiography the slab gels were stained with Coomassie blue, dried and placed on X-omat AR5 X-ray film (Kodak) at −80° C. for periods between 12 and 24 hours. The presence of radiolabelled G-like-proteins (generally of molecular weight between 39,000-55,000) indicated ADP-ribosylation had occurred.

We found that both the membrane and soluble (8 μg of total protein) fractions of Aplysia gonad totally inhibited ADP-ribosylation by cholera toxin (0.28 μg per μl) of G-proteins in membrane and soluble fractions of Aplysia taken from pooled ganglia from Aplysia (consisting of cerebral, pleural, pedal, and abdominal ganglion), and reproductive tract of Aplysia. That is, there was no detectable labelled G-protein even after 48 hours of exposure to X-ray film, indicating at least 90% inhibition of transferase activity, if not 100% inhibition. In addition, the autoribosylation of cholera toxin was inhibited by both membrane and soluble fractions of Aplysia gonad. For autoribosylation of cholera toxin the soluble fraction of gonad was more potent than the membrane fraction by at least an inhibitory factor of two. The soluble fraction of gonad also inhibits the CT ADP-ribosylation of G-proteins in the soluble and membrane fractions of rabbit liver and brain prepared, as described above, for Aplysia tissues. Further, the soluble fraction of Aplysia gonad inhibits the PT catalyzed ADP-ribosylation of G-proteins in the membrane fractions of Aplysia pooled ganglia, reproductive tract and rabbit liver and brain.

Referring to FIG. 1, the NAD cyclase was characterized further as a single, relatively sharp protein peak (with absorbance measured at 595 nm in a Coomassie blue binding assay) eluting at 300–400 mM NaCl from a cation exchange column (CM-SEPHAROSE-Cl-6B cation exchange resin) after the soluble fraction of gonad was bound to the resin. Approximately 5–10% of the total protein applied to the column bound to the resin, and 1% of the bound material was present as the single relatively sharp peak. Thus, a 1000-fold purification was achieved by a single cation exchange column step. The material in this protein peak totally inhibited CT-induced ADP-ribosylation of G-proteins of Aplysia pooled ganglia and reproductive tract assayed as described above. When the relatively sharp protein peak from the cation-exchange column was applied to a gel filtration column (SEPHACRYL-S200), the NAD cyclase eluted at 50–75% of the column volume.

Figure 2:
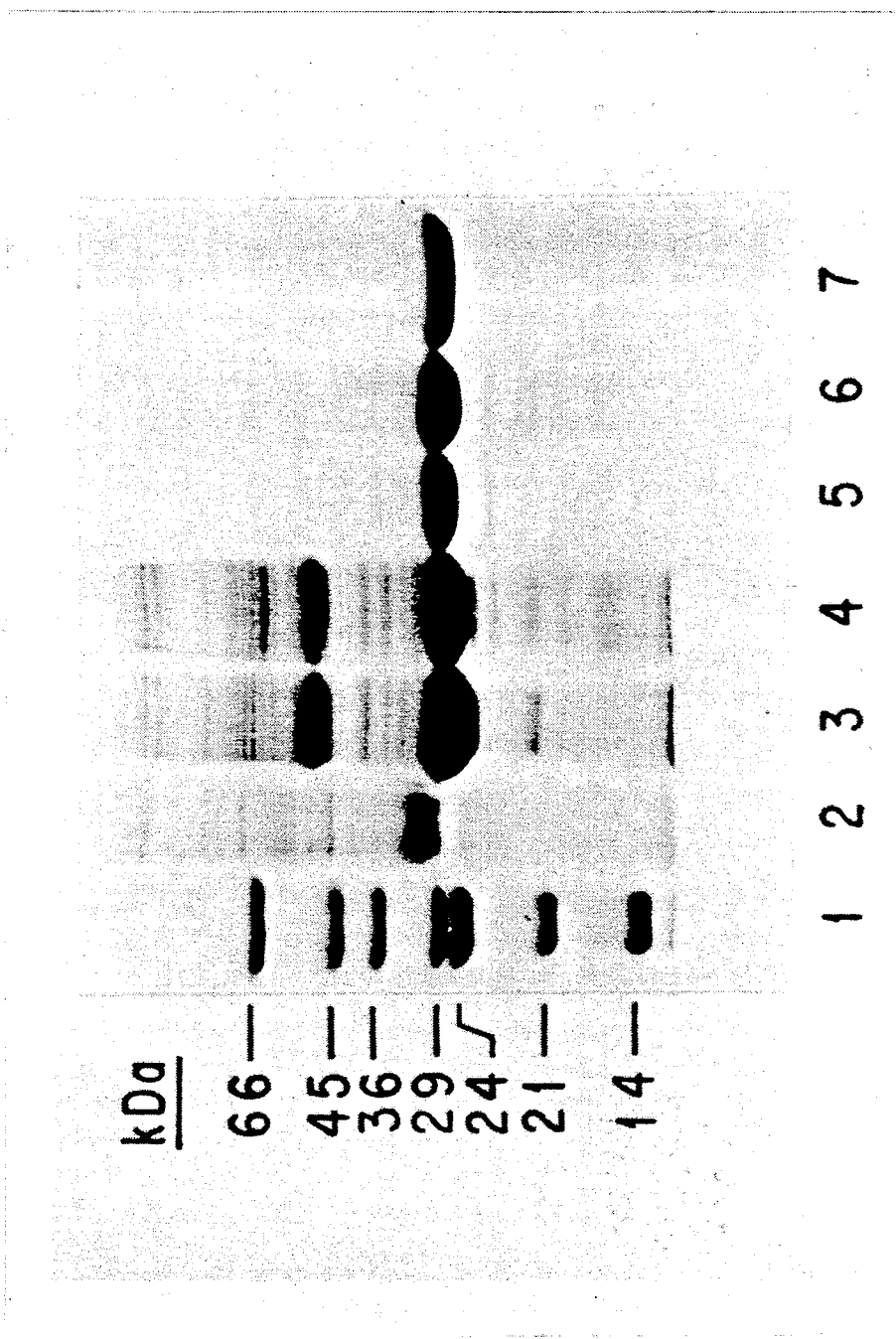
FIG. 2 is a photograph of a polyacrylamide gel stained with Coomassie blue showing the sequential stages of purification.

Referring to FIG. 2, this NAD cyclase has an apparent molecular weight in the range 24,000–34,000, with a predominant protein peak of apparent molecular weight 29,000 when separated by SDS-polyacrylamide gel electrophoresis (12% acrylamide, under reducing conditions, see below), is stained with Coomassie blue. FIG. 2 shows a Coomassie blue stained SDS-polyacrylamide gel (12% acrylamide) of the starting material and the peak ADP-ribosylation inhibitory activity from each column in a three step purification: (lane 1) Molecular weight markers [kDa=kilodaltons]; (lane 2) Aplysia ovotestis soluble fraction; (lane 3) peak from cation exchange column; (lane 4) starting material (after concentration) applied to the gel-filtration column; (lane 5) peak from the gel-filtration column; (lane 6) starting material (after concentration) applied to hydroxylapatite column; (lane 7) peak from the hydroxylapatite column.

In one example, twenty μl of the even-numbered fractions 20 through 52, eluted from the above cation-exchange column, by an NaCl gradient, were mixed with 20 μl of 2× Laemmli sample buffer (1.51 g Tris/HCl buffer, pH 6.8, 20 ml glycerol, 4 g SDS, 10 ml 2-mercaptoethanol, 0.002 g bromphenol blue, made up to a final volume of 100 ml with water). The 1× Laemmli sample buffer containing sample were heated for 1 min., in boiling water and loaded onto a 4% SDS-polyacrylamide stacking gel (pH 6.8) followed by a 12% separating slab gel (pH 8.7). The polyacrylamide gels were made from Bio-Rad premixed powder consisting of 37.5:1 acrylamide/Bis-acrylamide. The sample was electrophoresed through the stacking gel at 15–20 mamp, and through the separating gel at 35–50 mamp (4 hours for 11 cm×16 cm gels; 45 min. for 7 cm×10 cm gels with constant voltage at 200 V). 23 μg of a standard protein mixture obtained from Sigma (SDS-7) was applied to the standard lanes in the gel. The proteins were bovine albumin (66,000), egg ovalbumin (45,000), glyceraldehyde-3-phosphate dehydrogenase (36,000), carbonic anhydrase (29,000), trypsinogen (24,000), soybean trypsin inhibitor (20,100), alpha-lactalbumin (14,200). After electrophoresis, the gels were stained with 0.1% Coomassie blue in 50% methanol, 12% acetic acid. Destaining was performed in 50% methanol and 12% acetic acid. The molecular weight of the NAD cyclase was judged from its migration relative to the standard proteins.

Figure 3:
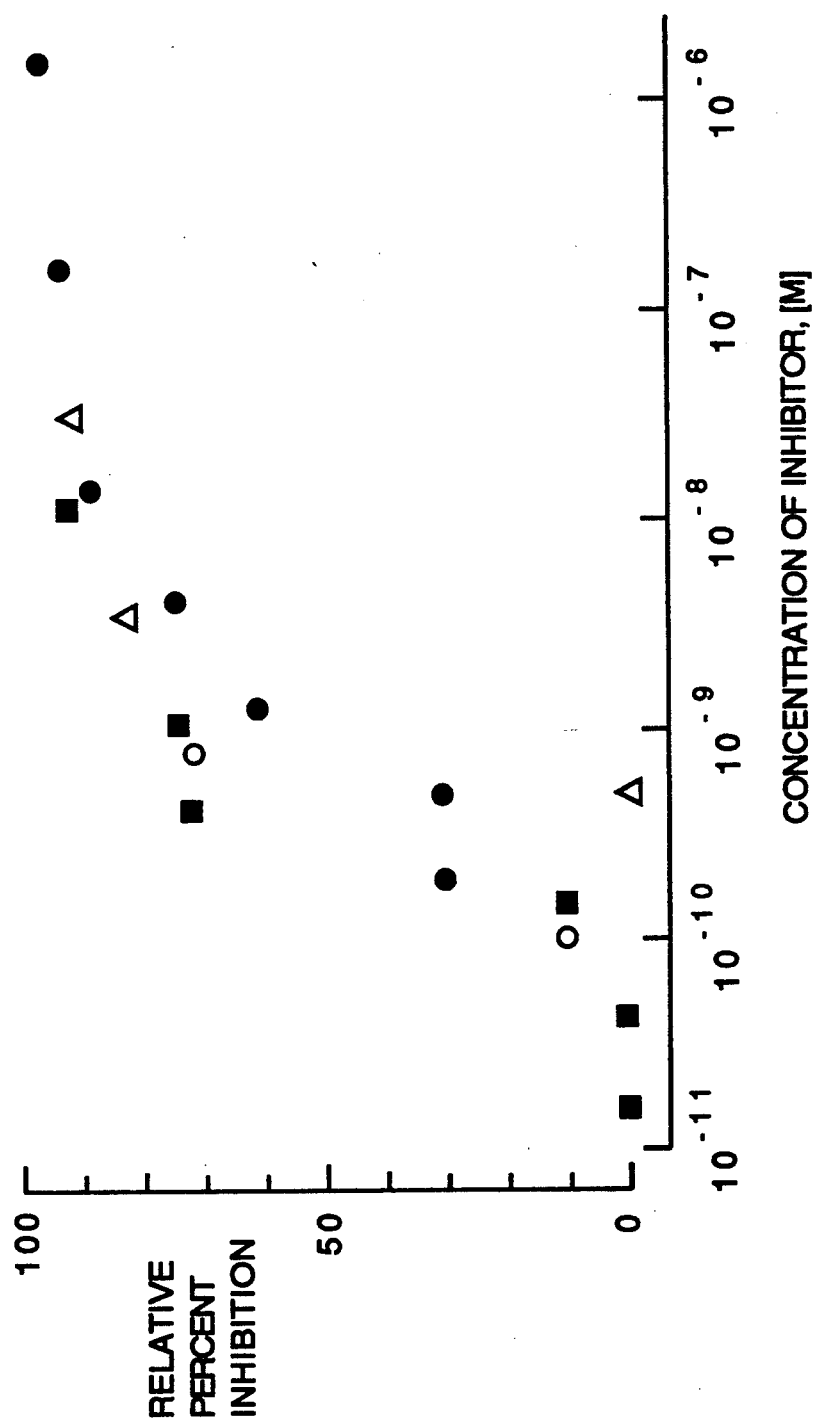
FIG. 3 is an $IC_{50}$ plot for Aplysia NAD cyclase.

Referring to FIG. 3, the NAD cyclase has an $IC_{50}$ of between 0.4 and 1 nanoMolar for CT- or PT-catalyzed ADP-ribosylation. Autoradiograms and the equivalent Coomassie-blue stained SDS-polyacrylamide gel were scanned by a microdensitometer (LKB Ultroscan XL laser Densitometer) in the region of interest (30 to 60 kDa). Normalization of the data for protein was achieved by dividing the range of optical density (O.D.) in the autoradiogram by the range of O.D. in the Coomassie-blue stained gel over the region of interest. The ratio of the inhibited reaction was then divided by the ratio of the control reaction (using heat-inactivated inhibitor), expressed as a percentage, and subtracted from 100%. Each symbol represents a different experiment.

Figure 4:
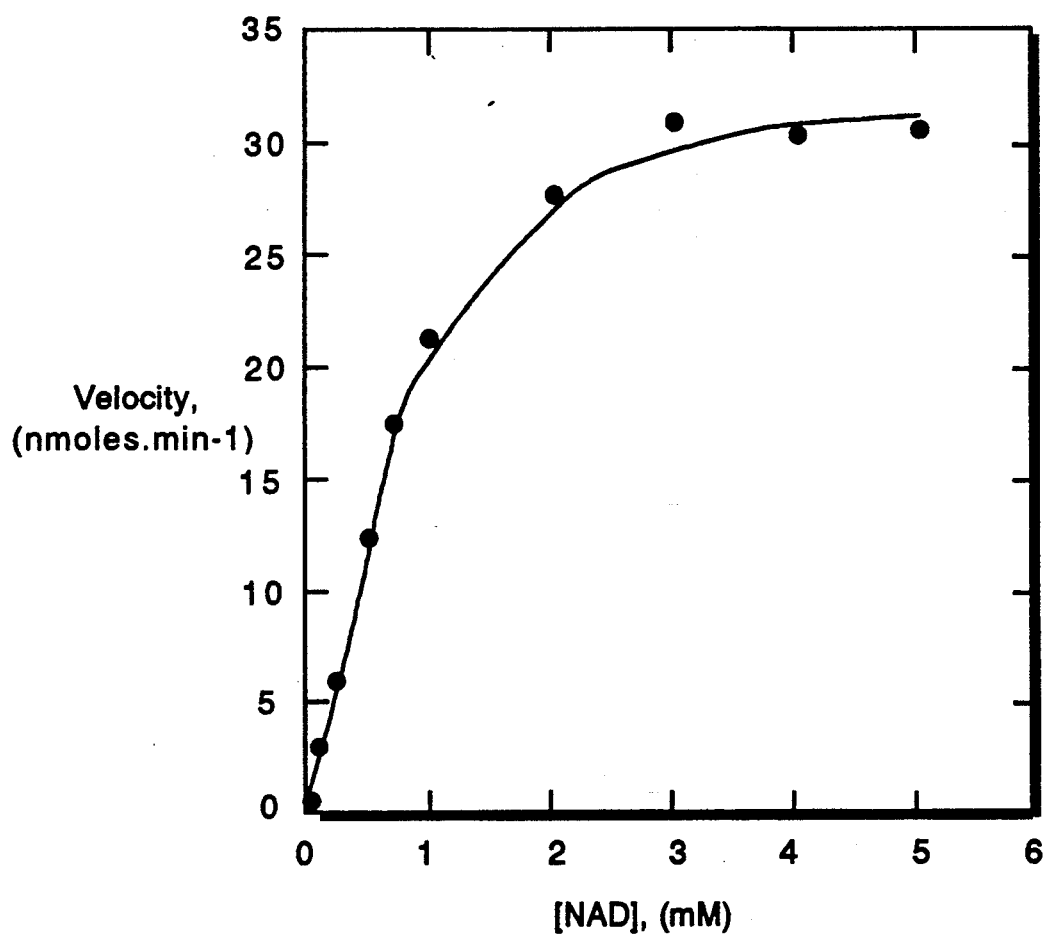
FIG. 4 is a plot of velocity of NAD cyclase reaction vs. NAD concentration.

Referring to FIG. 4, various concentrations (0.05 to 5.0 mM) of [carbonyl-$^{14}$C]NAD (specific activity=1.6 nCi/nmol) and $5\times 10^{-9}$M ovotestis NADase were incubated in 300 mM potassium phosphate buffer (pH 7.0) at 30° C. The amount of NAD cleaved during the incubation period was determined by measuring the amount of [$^{14}$C]-nicotinamide produced. The data was fitted to the equation $f=a+b*exp(-c*x)$ using a nonlinear curve fitting program (SigmaPlot, version 4.0). The estimated $K_m$ of the NAD Cyclase is 0.7 mM and the $V_{max}$ is approximately 32 nmoles/minute/35 ng enzyme. This corresponds to a turnover rate of about 27,000 moles NAD/minute/mole of NAD Cyclase at 30° C.

The molecular weight of cADPR was determined by mass spectrometry as follows. 2mM NAD was reacted with $1\times 10^{-7}$M purified NAD Cyclase (total volume 3 ml., in 20 mM potassium phosphate, pH 7.0) at 0° C. for 30 min. An equal volume of acetone was added at 30 min. to stop the reaction by precipitating protein. The solution was centrifuged at 20,000 g for 10 min. The supernatant was removed and the acetone was evaporated by a stream of $N_2$ gas. 2.5 ml of this solution was injected onto a Bio-Rad AG MP-1 anion exchange HPLC column and eluted with a linear gradient between 4 to 8% trifluoracetic acid in water (Lee et al., supra). cADPR eluted as a highly symmetrical peak in a total volume of 15 ml.

The 15 ml sample was aliquoted, as 1 ml samples, into microfuge (EPPENDORF) tubes. They were evaporated in a Speed-Vac concentrator (Savant) for four hours. This resulted in a five-fold concentration of the initial sample (final volume was 3 ml). An analytical run was made of 100 μl of this concentrate (15 min. retention time, (0.075 AU at 254 nm). cADPR was clearly present. Two 1 ml aliquots of the concentrate were evaporated to dryness in a Buchler vortex evaporator for four hours. 200 μl of water was added to each of the resulting tubes, and these were pooled and re-aliquoted. These two samples (200 μl each) were frozen. One was thawed and 50 μl was removed for analysis by HPLC, as described above. The elution profile of cADPR was normal (15 min. retention time, 0.14 AU at 254 nm). The second frozen sample was used for determination of molecular weight by mass spectrometry.

Analysis of the sample, in order to obtain molecular weight was performed by negative ion fast atom bombardment (FAB−) at the Massachusetts Institute of Technology Mass Spectrometry Facility. Glycerol was used as the matrix. A single peak was observed with mass (−H) of 540. This agrees with the calculated m.w. of cADPR with one less H.

The NAD cyclase is sensitive to heating at temperatures of 70°-95° C. for 15-60 minutes just prior to an ADP-ribosylation assay.

HPLC analysis of the NAD cyclase product was performed as follows. The products generated by the purified NAD cyclase after incubation with NAD were separated on a Vydac 303NT405 column (0.46×5 cm). Samples to be separated on the HPLC were prepared as follows: At t=0, 1×10$^{-7}$M purified NAD cyclase was added to 2 mM NAD in 20 mM potassium phosphate buffer, pH 7.0. After incubation at 0° C. for 1 to 15 minutes the reaction was stopped by the addition of an equal volume of acetone (100 μl) and incubated on ice an additional 10-15 min. The precipitated protein was removed by centrifugation (14,000×g at 4° C. for 10 minutes) and the acetone evaporated from the supernatant under a stream of nitrogen gas. The pH of the supernatant was neutralized by the addition of 100 μl of 20 mM potassium phosphate buffer pH 7.0. In order to separate the enzyme products, a protocol established by Lee et al., (supra) was used except that ammonium acetate was substituted for ammonium formate in solvent A, and acetic acid for formic acid in solvent B. 20 μl of the sample was then injected onto the Vydac 303NT405 column, equilibrated with 0.045M CH$_3$COONH$_4$ (solvent A), pH 4.6 with H$_3$PO$_4$, and eluted with a linear gradient from 0-100% 0.5M NaH$_2$PO$_4$ (solvent B), pH 2.7 with CH$_3$COOH in 10 minutes at a flow rate of 2 ml/min. Sample elution from the column was monitored at 254 nm. Control samples (minus NAD cyclase) containing known standards (nicotinamide, NAD, ADPR and ADP) were treated as described above.

Figure 5:
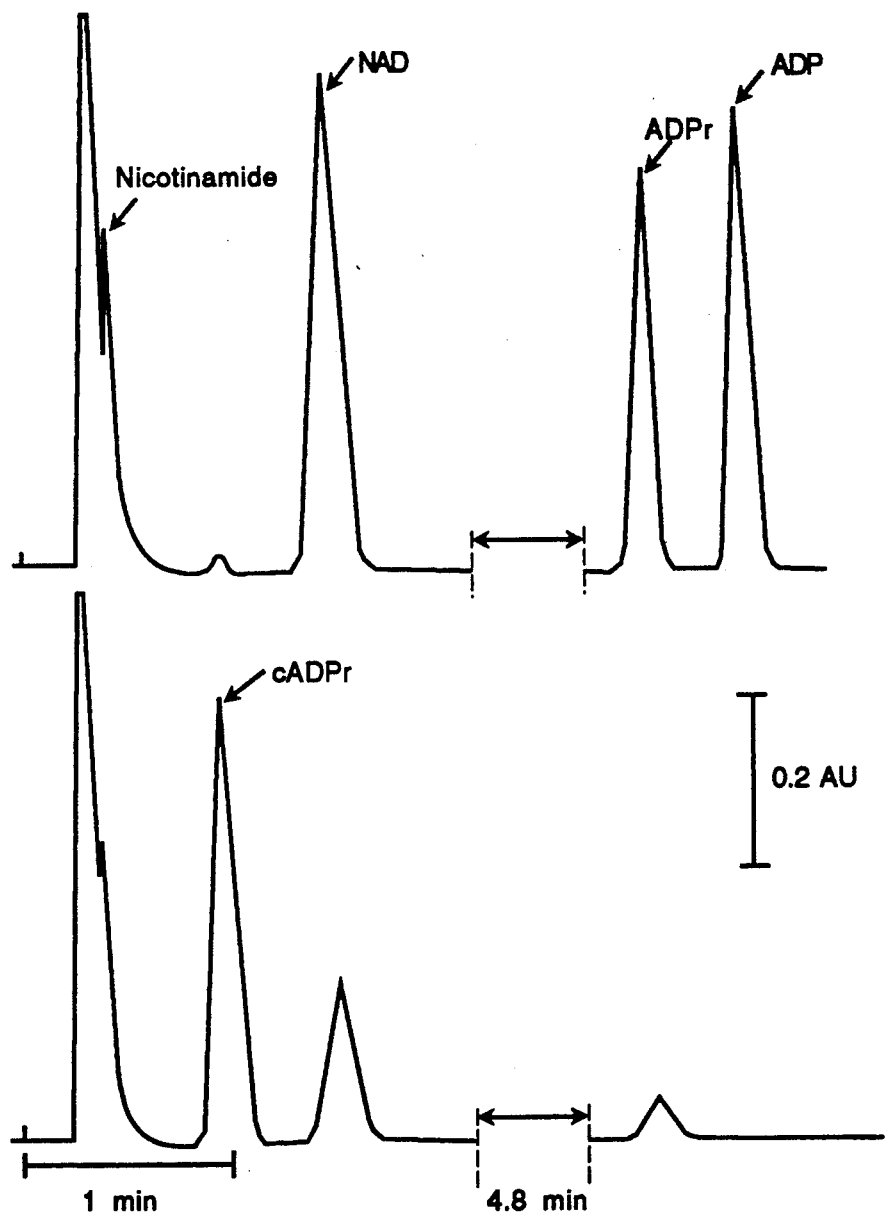
FIG. 5 is an HPLC chromatograph of products generated by Aplysia NAD cyclase from NAD.

The products of the NAD cyclase were characterized by adding the purified enzyme to an NAD/buffer mixture for 1, 5 or 15 minutes (0° C.), stopping the reaction and separating the products on an ion exchange column, using HPLC, as described above. FIG. 5 illustrates two HPLC traces, the top trace showing the elution profile of the standards (nicotinamide, NAD, ADPR, and ADP, in that order; nicotinamide, retention time (rt)=0.4 min.; NAD, rt=1.5 min.; ADPR, rt=7.4 min.; ADP, rt=8.1 min.), and the bottom trace showing the products after 5 minutes (cADPR, rt=1.0 min). The major product, cADPR, elutes between nicotinamide and NAD. After 1 and 15 minutes, cADPR accounts for 97% and 87%, respectively, of the sum of the two products (cADPR and ADP-R). 3.8 mg (7 μmoles) of purified cADPR can be generated in the above reaction in 15 minutes (at 0°).

The purity of the cADPR was also judged by HPLC using a C$_{18}$ column (Vydac). cADPR collected from the first column was lyophilized, dissolved in ultrapure water and injected onto the C18 column equilibrated with 6.6 mM formic acid. The column and conditions were identical to Lee et al., supra. Absorbance monitoring was at 260 nm. Two peaks appeared in the absorbance tracing. The first peak was contaminating nicotinamide and the second larger peak was cADPR. cADPR accounted for about 85% of the total material loaded onto the column.

The identity of the NAD cyclase product was further shown to be cADPR by proton NMR, and by a study of its calcium releasing properties.

The substrate specificity of the Aplysia NAD cyclase was investigated by incubating the enzyme with 1 mM of various NAD+ analogs at pH 7.0 for 1 min and assayed for production of cADPR using the calcium release assay. Analogs tested were α- and β-NAD+, ADP-ribose, NADH, NADP, NADPH, nicotinamide mononucleotide, deamino NAD+, and nicotinic acid adenine dinucleotide. Only NADH partially substitutes for β-NAD+. ADP-ribose is not a substrate, indicating that the enzyme directly cyclized NAD+ into cADPR instead of going through ADP-ribose as an intermediate step. The reaction is stereospecific since α-NAD+ is not a substrate.

In addition to Aplysia ovotestis, activity of the NAD cyclase can be detected also in sea urchin egg as well as a variety of mammalian tissue extracts indicating it is an ubiquitous enzyme. Both the Aplysia and the mammalian NAD cyclase share the same high degree of substrate specificity.

The above described NAD cyclase, or other related and equivalent NAD cyclases, can be readily purified as described above and indeed purified to homogeneity in sufficient concentration to allow the amino acid sequence of all or a part of the NAD cyclase to be determined. This can be performed by standard procedures. For example, other NAD cyclases can be readily identified, isolated and purified as described above. In one method, such enzymes can be identified by their ability to produce cADPR from exogenously added NAD. The cADPR is identified by HPLC analysis as described above. The protein having such activity can be identified after column chromatography. One example of such methodology to identify such a protein is preparing squid (*LoRigo pealei*) brain homogenate, passing the aqueous-soluble extract over a cation exchange column (e.g., WATERS ACELL-CM resin) and eluting with NaCl. One broad peak of protein elutes which has the cADPR-producing activity. This protein can be readily purified further by standard technique.

Such isolated and purified proteins permit the determination of a series of oligonucleotide sequences which encode for the isolated amino acid sequence, and thus can be used as a hybridization probe for a genomic or cDNA library containing, for example, Aplysia DNA, or DNA from other organisms. Genes encoding the NAD cyclase can then be isolated by standard procedure. Once such a gene has been cloned, it may be sequenced by standard technique and the DNA placed within any standard expression vector, for example, λgt11 to cause expression of the cloned gene in *E. coli* or other bacteria. Alternatively, other standard vectors may be used to cause expression of the gene within yeasts, or other eucaryotic systems, such as mammalian tissue culture cells. Such expression will cause production of a recombinant NAD cyclase. In addition, once the polypeptide sequence of an NAD cyclase is determined, a synthetic polypeptide including the eucaryotically active part of the NAD cyclase may be synthesized. An example of such cloning techniques now follows.

In order to clone the gene for the above-described NAD cyclase, total RNA was isolated from the ovotestis of *Aplysia californica* using 4M guanidinium thiocyanate and phenol at 60° C. The mRNA was purified by affinity chromatography over an oligo-dT cellulose column. After two passes over oligo-dT cellulose, no traces of rRNA was seen, and mRNA up to 9 kB in length was detected.

First strand cDNA was made from the ovotestis mRNA using Moloney Murine Leukemia Virus reverse transcriptase and random primers. Second strand cDNA was then made with RNAse H and *E. coli* polymerase I. The cDNA was blunt ended with T4-polymerase and NotI:EcoRI adapter-linkers ligated to the blunt ends. The cDNA was size selected over a BioRad A-50 column to obtain cDNA greater than 500 base pairs, and then ligated into EcoRI-restricted lambda gt10 arms. The resulting lambda DNA (containing inserts) was then packaged with Stratagene gigapack gold packaging mix to provide a cDNA library of approximately $1 \times 10^7$ recombinants.

The library was plated at a density of 40,000 plaques per plate and plaque lifts were taken with nitrocellulose filters. The filters were probed with two oligonucleotides that correspond to the N-terminal amino acid sequence of the NAD cyclase (DG-2) or an internal amino acid sequence (DG-1). Both these amino acid sequences were obtained by standard procedure. The oligonucleotide probes are shown below:

(ID SEQ. NO.: 1).:
```
DG-1  5' TAT GAT GAA GCI CAT GAT TAT GC 3'
           C   C   G       G   C   C
```

(ID SEQ. NO.: 2):
```
DG-2  5' TGT AAA GAT TAT GAA ATI AC        3'
           C   G   C   C   G
```

Hybridization of the filters with DB-1 was at 25° C., 6× SSC, while hybridization with DG-2 was at 20° C., 9× SSC. Filters were washed at 37° C. in 6× SSC for DG-1, and at 27° C. in 9×SSC for DG-2. Secondary and tertiary screens of positive plaques were at higher stringency to eliminate false positives: DG-1 positive plaques were hybridized at 41° C. in 6× SSC, 20% formamide, while DG-2 positive plaques were hybridized at 31° C. in 6× SSC, 20% formamide. The DG-1 filters were washed at 51° C. in 2× SSC and the DG-2 filters were washed at 31° C. in 6× SSC.

Three positive clones that hybridized strongly with DG-1 were purified and designated as NAD cyclase clones: S3, 03, and K. The cloned insert sizes were approximately 700 bp for K, 800 bp for S3 and 1000 bp for 03. The insert DNA was cut out of the lambda vector with EcoRI and subcloned into M13mp18 for sequencing purposes. DNA sequences of 03 are given below, excluding all of the 5' region prior to the N-terminal amino-acid of the NAD cyclase (see ID SEQ. NO.: 3): (The amino acid sequence shown below is shown as the standard single letter amino acid code.)

```
GATTTAGAAATGTCTCCCGTCGCCATTATTGCTTGTGTGTGTCTGGCGGTGACGCTGACA    60
           M  S  P  V  A  I  I  A  C  V  C  L  A  V  T  L  T    17
AGTATCTCGCCCAGCGAGGCCATCGTCCCCACTCGCGAGTTGGAGAATGTGTTCCTTGGC    120
 S  I  S  P  S  E  A  I  V  P  T  R  E  L  E  N  V  F  L  G    37
CGCTGTAAGGATTACGAGATCACCCGATACCTGGATATTCTTCCCAGAGTGAGATCGGAC    180
 R  C  K  D  Y  E  I  T  R  Y  L  D  I  L  P  R  V  R  S  D    57
TGCTCGGCATTGTGGAAGGACTTTTTTCAAAGCCTTCTCCTTCAAAAATCCCTGTGATCTC   240
 C  S  A  L  W  K  D  F  F  K  A  F  S  F  K  N  P  C  D  L    77
GACCTTGGAAGTTACAAAGATTTTTTCACTAGTGCGCAACAGCAGCTGCCAAAGAACAAA   300
 D  L  G  S  Y  K  D  F  F  T  S  A  Q  Q  Q  L  P  K  N  K    97
GTAATGTTCTGGTCTGGAGTCTATGACGAGGCTCACGATTATGCCAACACCGGCAGGAAG   360
 V  M  F  W  S  G  V  Y  D  E  A  H  D  Y  A  N  T  G  R  K   117
TACATCACTTTGGAAGATACGCTTCCGGGTTACATGTTGAACTCTCTGGTTTGGTGCGGC   420
 Y  I  T  L  E  D  T  L  P  G  Y  M  L  N  S  L  V  W  C  G   137
CAACGCGCTAATCCAGGATTCAACGAAAAGGTGTGCCCGGACTTCAAAACGTGTCCAGTG   480
 Q  R  A  N  P  G  F  N  E  K  V  C  P  D  F  K  T  C  P  V   157
CAAGCTAGAGAGAGCTTCTGGGGAATGGCGTCAAGTTCTTATGCTCACAGTGCAGAGGGA   540
 Q  A  R  E  S  F  W  G  M  A  S  S  S  Y  A  H  S  A  E  G   177
GAAGTGACCTACATGGTCGACGGTTCGAATCCCAAGGTACCAGCTTACAGGCCAGACAGT   600
 E  V  T  Y  M  V  D  G  S  N  P  K  V  P  A  Y  R  P  D  S   197
TTTTTTGGCAAGTACGAACTGCCCAATCTGACTAACAAGGTGACAAGGGTAAAGGTCATC   660
 F  F  G  K  Y  E  L  P  N  L  T  N  K  V  T  R  V  K  V  I   217
```

```
GTCCTGCATCGGCTCGGGGAAAAGATCATAGAGAAGTGCGGTGCAGGATCTTTGCTGGAC    720
 V   L   H   R   L   G   E   K   I   I   E   K   C   G   A   G   S   L   L   D    237

CTTGAAAAGCTTGTCAAAGCCAAGCATTTTGCATTCGATTGCGTGGAAAATCCAAGGGCT    780
 L   E   K   L   V   K   A   K   H   F   A   F   D   C   V   E   N   P   R   A    257

GTTCTCTTCTTGCTGTGCTCCGACAACCCCAATGCCAGAGAGTGTCGACTCGCTAAACGT    840
 V   L   F   L   L   C   S   D   N   P   N   A   R   E   C   R   L   A   K   R    277

TTCTACAGGATCGCCTAAATAATCCAGCACCGCTCGTCAACTATTTAAGAGGCGTTTCGT    900
 F   Y   R   I   A   stop                                                         282

TAGAGGTTTATAAATTAATTCTTTTTTTTTTGAGAACGTGTCGACGGTGGCAAAATGGGGT    960

CGTTTTTTTAGTCATTAGTGTTGGAAAATATATTGGGGATAAAAATGGGGTGGGGCTGGG   1020

GCATTGCTGTTGACGATATAAAGTAAAGAGGGAGGGGGCAGCTCTTCACTTCAGTGCGCA   1080

CAGCAGTTGTTATGAATTGAGGGCTGAACGTTCTCGAGTACATTTCAATATTAACTTCTT   1140

GATGTAGAGAGGGTACGCTCTTTACCAATTTCAAATTATTTAAAAGGTGTG            1191
```

This DNA sequence (which is listed as GenBank accession number M37644) is sufficient to allow a person of ordinary skill to isolate a full length cDNA or genomic clone from an existing library, or one constructed as described above. This full length clone can be inserted into any standard mammalian expression system to provide useful recombinant NAD cyclase.

USES

The NAD cyclases are useful for producing purified cADPR, as described above. The NAD cyclases of this invention are the only purified enzymes that can presently generate cADPR.

cADPR is useful for causing release of calcium ions from internal stores in cells. Such release of calcium ions can cause cellular death. $Ca^{2+}$ is of enormous importance in biological systems playing crucial roles in many cellular functions including early events after fertilization, muscle contraction, secretion of neurotransmitters, hormones and other compounds, and as a second messenger activating various enzymes. cADPR is as potent as $IP_3$ in releasing $Ca^{2+}$ from intracellular stores. Thus, cADPR can replace $IP_3$ use in therapy and research.

cADPR receptors may be identified by use of the purified cADPR using standard techniques. Radioactive cADPR can be synthesized from radioactive NAD and used as a ligand to identify and localize receptors for cADPR. Such receptors on the outer surfaces of cells operate $ca^{2+}$-channels in the external membrane. Analogs of cADPR can be developed that block the affect of cADPR on such cADPR-receptors. These blocking analogs are useful to block the normal influence of naturally occurring cADPR. Such analogs are thus useful pharmaceutical agents for diseases, such as hypertension.

An immunodetection kit for cADPR can be formed using the purified cADPR. After coupling cADPR to a protein carrier (e.g., bovine serum albumin or limpet haemocyanin), antibodies can be made to the complex and selected (using standard monoclonal antibody generating techniques) to have a high specificity for cADPR (versus ADP-R). An immunodetection kit containing such an antibody is useful in basic research and for clinical tests or diagnosis of disease characterized by the presence of $Ca^{2+}$ imbalance The NAD cyclase is useful for causing localized production of cADPR, or cADPR may be itself locally administered, for example, to cancer cells to cause the specific death of such cancer cells. cADPR can be readily modified so that it will be permeable to the cell membrane. Such modified cADPR provides a means to induce release of intracellular $Ca^{2+}$, which will activate $Ca^{2+}$-sensitive proteases and destroy affected cells. Direct injection of membrane-permeable-cADPR into a tumor is an efficient method of getting the compound to the tumor (and thereby kill tumor cells), although other more sophisticated delivery systems (such as directed tumor receptor targeting) can be developed.

The NAD cyclases of this invention are also useful for routine assays of chemicals and enzymes. For example, assay for NAD, or enzymes which required NAD for activity.

These NAD cyclases are also useful as attractants or affinity agents for bacteria, and can be used as therapeutic for reducing bacterial infection. For example, a gene encoding an NAD cyclase can be inserted into a mammalian cell (e.g., a macrophage, such as a Kupffer cell, or other cells involved in phagocytosis of foreign material, including bacteria, which have access to bacterial cells) under appropriate control to cause expression of the NAD cyclase as an ectoprotein (i.e., on the outer surface of the cell) in order to attract bacteria to the cell which may then engulf and destroy the bacteria, as described by Amar-Costesec et al., 100 J. Cell. Biol. 189, 1985.

Other embodiments are within the following claims.

We claim:

1. A purified deoxyribonucleic acid comprising the nucleic acid sequence shown as SEQ. ID NO. 3.

* * * * *